United States Patent [19]
De Nanteuil et al.

[11] Patent Number: 6,114,360
[45] Date of Patent: Sep. 5, 2000

[54] PYRROLE COMPOUNDS

[75] Inventors: Guillaume De Nanteuil, Suresnes; Bernard Portevin, Elancourt; Jacqueline Bonnet, Paris; Charles Tordjman, Boulogne, all of France

[73] Assignee: Adir et Compagnie, Courbevoie, France

[21] Appl. No.: 09/390,416

[22] Filed: Sep. 3, 1999

Related U.S. Application Data

[62] Division of application No. 09/199,640, Nov. 25, 1998.

[30] Foreign Application Priority Data

Nov. 26, 1997 [FR] France ................. 97.14840

[51] Int. Cl.[7] ............... A61K 31/4035; C07D 401/04
[52] U.S. Cl. .................... 514/339; 546/277.1
[58] Field of Search ............. 546/277.1; 514/339

[56] References Cited

PUBLICATIONS

Von Dobenek et al., CA 71:124155, 1969.

*Primary Examiner*—Joseph McKane
*Assistant Examiner*—Sonya Wright
*Attorney, Agent, or Firm*—The Firm of Gordon W. Hueschen

[57] ABSTRACT

Compounds of formula (I):

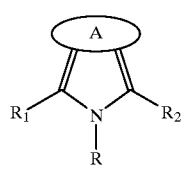

wherein:

R represents hydrogen, alkyl, optionally-substituted amino, or linear or branched ($C_1$–$C_6$)-acyl, $R_1$ and $R_2$, which may be identical or different, each represents independently of the other aryl, heteroaryl, or ($C_5$–$C_7$)-cycloalkyl, or one of those groups optionally substituted, A, together with the atoms in common with the pyrrole, represents saturated or unsaturated, monocyclic or bicyclic ($C_3$–$C_{12}$)-cycloalkyl, or a saturated heterocycle having 5 to 7 ring members and containing one or two nitrogen, or 7-oxabicyclo[2.2.1]heptane, or one of those groups optionally substituted, their isomers, and also addition salts thereof with a pharmaceutically-acceptable acid or base, pharmaceutical compositions thereof, and use thereof as medicaments.

9 Claims, No Drawings

PYRROLE COMPOUNDS

The present application is a division of our prior-filed copending application Ser. No. 09/199,640, filed Nov. 25, 1998, now allowed.

FIELD OF THE INVENTION

The present invention relates to new pyrrole compounds.

A number of pyrrole compounds having a dihydro- or tetrahydro-isoindole structure are described in the literature. Of those, attention may be drawn to compounds containing in the 1 and 3 positions a phenyl group (*Bull. Chem. Soc. Jp.*, 1993, 66 (9), 2707–2713), a substituted phenyl group (*Chem. Ber.*, 1972, 105, 1258–1278), or a phenyl group and an isoquinoline (*J. Org. Chem.*, 1981, 46, 1656; *Bull. Soc. Chem. Belges*, 1992, 101 (2), 109–112). Those particular compounds are disclosed in those documents through their method of synthesis or their spectral characteristics. No therapeutic activity is known or disclosed for those compounds.

The novelty of the compounds of the invention, in addition to the fact that they are new, lies in their selective inhibitory activity in relation to cyclooxygenase-2 (COX 2) and of inducible nitric oxyde synthase (iNOS)

The prostaglandins (PG) play an important role in the development of inflammatory reactions. Since the discovery by Vane in 1971 (*Nature*, 1971, 321, 232–235), who made an association between the activity of non-steroidal anti-inflammatories (NSAIs) and inhibition of the cyclooxygenase pathway of the arachidonic cascade, inhibition of the production of PGs constitutes the main target in the discovery of compounds having an anti-inflammatory activity.

However, compounds active against the pain and inflammation induced by PGs are also inhibitors of physiological processes that are regulated by PGs independently of the inflammatory reaction, and hence produce undesirable side effects such as gastric ulcers and/or effects on the kidneys.

The discovery of an isoenzyme of cyclooxygenase (COX) in 1991 (*J. Biol. Chem.*, 1991, 266, 12866–12872; *Proc. Natl Acad. Sci. USA*, 1991, 88, 2692–2696) made it possible to establish the difference between constitutive COX (COX 1), which is widely distributed in the organism, especially in the stomach and the kidneys, and inducible COX (COX 2), the synthesis of which is induced by inflammatory and mitogenic stimuli. The hypothesis has thus been put forward that a selective inhibitor of COX 2 might be a powerful anti-inflammatory compound without gastrointestinal and/or renal side-effects.

Interleukin 1β (IL1β) is produced by macrophages and is the dominant factor of a large number of inflammatory processes. In particular, IL1β stimulates the cells that synthesise and express COX 2, yielding PGs. IL1β is also responsible for the expression and synthesis of inducible NO synthase and of the proteases that are involved in the degradation of the extracellular matrix of cartilage.

The inflammatory processes mediated by the COXs are common to a large number of pathologies. They play an important role in rheumatology and especially in rheumatoid arthritis and arthrosis. The inhibition of COX 2 has been proposed for limiting the inflammatory reactions occurring in the development of those pathologies. The inhibition of IL1β also constitutes a target that allows regulation of, on the one hand, the inflammation and, on the other hand, the articular degradation characteristic of those pathologies.

In addition to the fact that the compounds of the present invention are new, they have proved to be specific inhibitors of COX 2, IL1β and iNOS, making them potentially useful in the treatment of the inflammatory processes that occur especially in rheumatic disorders, such as arthrosis and rheumatoid arthritis, but also in atherosclerosis, cancer, etc.

DETAILED DESCRIPTION OF THE INVENTION

The present invention relates more especially to the compounds of formula (I):

wherein:
R represents:
  a hydrogen atom,
  a linear or branched $(C_1-C_6)$-alkyl group optionally substituted by one or more, identical or differents groups selected from hydroxy, linear or branched $(C_1-C_6)$-alkoxy, carboxy and linear or branched $(C_1-C_6)$-alkoxycarbonyl groups,
  an amino group optionally substituted by one or two identical or different groups selected from linear or branched $(C_1-C_6)$-alkyl, linear or branched $(C_1-C_6)$-alkoxycarbonyl, linear or branched aryl-$(C_1-C_6)$-alkoxycarbonyl, linear or branched $(C_1-C_6)$-alkylsulphonyl and arylsulphonyl,
  or a linear or branched $(C_1-C_6)$-acyl group,
$R_1$ and $R_2$, which may be identical or different, each represents aryl, heteroaryl or $(C_3-C_7)$-cycloalkyl group, it being possible for each of those $R_1$ or $R_2$ groups optionally to be substituted by one or more identical or different groups selected from:
  halogen,
  linear or branched $(C_1-C_6)$-alkyl optionally substituted by one or more halogen atoms, hydroxy groups, linear or branched $(C_1-C_6)$-alkoxy groups, amino groups or linear or branched $(C_1-C_6)$-alkoxycarbonyl groups,
  linear or branched $(C_1-C_6)$-alkoxy optionally substituted by an amino group that is itself optionally substituted by one or two identical or different linear or branched $(C_1-C_6)$-alkyl groups,
  linear or branched $(C_1-C_6)$-trihaloalkoxy,
  linear or branched $(C_1-C_6)$-acyl,
  hydroxy, nitro, cyano, mercapto, carboxy,
  amino optionally substituted by one or two identical or different groups selected from linear or branched $(C_1-C_6)$-alkyl, linear or branched $(C_1-C_6)$-alkylcarbonyl and linear or branched $(C_1-C_6)$-alkylsulphonyl,
  linear or branched $(C_1-C_6)$-alkoxycarbonyl,
  linear or branched $(C_1-C_6)$-alkylthio,
  sulphonyl substituted by a linear or branched $(C_1-C_6)$-alkyl group or an amino group which is optionally substituted by one or two identical or different linear or branched $(C_1-C_6)$-alkyl groups, and
  a saturated or unsaturated, monocyclic or bicyclic heterocycle having from 5 to 10 ring members and containing 1, 2 or 3 identical or different hetero atoms selected from nitrogen, oxygen and sulphur, optionally substituted by one or more identical or different groups selected from halogen, linear or branched ($C_1$–$C_6$)-alkyl and linear or branched ($C_1$–$C_6$)-alkoxy, A represents, together with the atoms in common with the pyrrole:
- a saturated or mono unsaturated, monocyclic or bicyclic ($C_3$–$C_{12}$)-cycloalkyl group,
- a saturated heterocycle having from 5 to 7 ring members and containing one or two nitrogen atoms,
- or a 7-oxabicyclo[2.2.1]heptane radical, it being possible for each of those rings optionally to be substituted by one or more identical or different groups selected from:
  halogen,
  trihalomethyl,
  linear or branched ($C_1$–$C_6$)-alkyl optionally substituted by one or more halogen atoms or hydroxy groups,
  linear or branched ($C_1$–$C_6$)-alkoxy,
  linear or branched ($C_1$–$C_6$)-aminoalkyl,
  cyano,
  aryl or linear or branched aryl-($C_1$–$C_6$)-alkyl, it being possible for the aryl moiety of the said groups optionally to be substituted by one or more identical or different groups selected from halogen, hydroxy, linear or branched ($C_1$–$C_6$)-alkyl and linear or branched ($C_1$–$C_6$)-alkoxy,
  and sulphonyl substituted by a linear or branched ($C_1$–$C_6$)-alkyl group or an amino group itself optionally substituted by one or two identical or different linear or branched ($C_1$–$C_6$)-alkyl groups, it being understood that:
  an aryl group denotes a phenyl or naphthyl group, and a heteroaryl group denotes an aryl group containing one, two or three identical or different hetero atoms selected from nitrogen, oxygen and sulphur, their isomers, and also addition salts thereof with a pharmaceutically acceptable acid or base, provided that:
  when A, together with the atoms in common with the pyrrole ring, is a cyclohexane or a norbornene and R is a hydrogen atom, $R_1$ and $R_2$ cannot simultaneously each represent a phenyl group,
  when $R_1$ represents a phenyl group, R represents a hydrogen atom
    and when $R_2$ represents a para-nitrophenyl group, then A, together with the atoms in common with the pyrrole ring, cannot represent a norbornane,
    or when $R_2$ represents a 1-isoquinolyl group, then A, together with the atoms in common with the pyrrole ring, cannot represent a cyclohexane or a 1,2-indanyl group;

and provided also that:
  if $R_2$ represents a 4-pyridyl or 4-quinolyl group, each of those groups optionally being substituted by one or more groups selected from halogen, linear or branched ($C_1$–$C_6$)-alkyl (itself optionally substituted by a hydroxy or linear or branched ($C_1$–$C_6$)-alkoxy group), hydroxy, nitro, amino, linear or branched ($C_1$–$C_6$)-acyl and linear or branched ($C_1$–$C_6$)-alkoxycarbonyl,
  and $R_1$ represents a phenyl, naphthyl, pyridyl or quinolyl group, each of those groups optionally being substituted by one or two groups selected from halogen, linear or branched ($C_1$–$C_4$)-alkyl (itself optionally substituted by a halogen atom), linear or branched ($C_1$–$C_4$)-alkoxy, nitro, hydroxy, amino (optionally substituted by one or two linear or branched ($C_1$–$C_6$)-alkyl groups), linear or branched ($C_1$–$C_4$)-alkoxycarbonyl and linear or branched ($C_1$–$C_4$)-alkylthio,
  then A, together with the atoms in common with the pyrrole ring, cannot represent a saturated monocyclic ($C_5$–$C_8$)-cycloalkyl group or a saturated heterocycle having from 5 to 7 ring members and containing 1 or 2 nitrogen atoms, each of such groups optionally being substituted by one or two groups selected from linear or branched ($C_1$–$C_6$)-alkyl, linear or branched ($C_1$–$C_4$)-alkoxy, and aryl.

Advantageously, the preferred compounds of the invention are those of formula (I) wherein:
  $R_1$ and $R_2$, which may be identical or different, each represents independently of the other an aryl group optionally substituted by one or more of any of the groups as defined hereinabove, advantageously by one or more halogen atoms,
  and A represents, together with the atoms in common with the pyrrole ring, a monocyclic or bicyclic ($C_3$–$C_{12}$)- or advantageously ($C_5$–$C_8$)-cycloalkyl group that is saturated or unsaturated but not of aromatic character, optionally substituted by one or more of any of the substituents as defined hereinabove, their isomers, and also addition salts thereof with a pharmaceutically acceptable acid or base.

Especially advantageously, the preferred compounds of the invention are those of formula (I) wherein A represents, together with the atoms in common with the pyrrole ring, a bicyclic ($C_5$–$C_{12}$)- or advantageously ($C_5$–$C_8$)-cycloalkyl group that is saturated or unsaturated but not of aromatic character, optionally substituted by one or more of any of the groups as defined hereinabove, their isomers, and also addition salts thereof with a pharmaceutically acceptable acid or base.

According to another advantageous variant of the invention, the preferred compounds are those of formula (I) wherein:
  $R_1$ and $R_2$, which are identical, each represents a heteroaryl group optionally substituted by one or more of any of the groups as defined hereinabove,
  and A represents, together with the atoms in common with the pyrrole ring, a bicyclic ($C_5$–$C_{12}$)- or advantageously ($C_5$–$C_8$)-cycloalkyl group that is saturated or unsaturated but not of aromatic character, optionally substituted by one or more of any of the groups as defined hereinabove, their isomers, and also addition salts thereof with a pharmaceutically acceptable acid or base.

Finally, very advantageously the preferred compounds of the invention are the following compounds of formula (I):
  1,3-di-(4-fluorophenyl)-4,5,6,7-tetrahydro-2H-isoindole,
  1,3-diphenyl-5,6-dimenthyl-4,5,6,7-tetrahydro-2H-isoindole,
  1,3-diphenyl-4,7-methano4,5,6,7-tetrahydro-2H-isoindole,
  1,3-di-(4-fluorophenyl)-2,4,5,6-tetrahydrocyclopenta[c]pyrrole,
  1,3-diphenyl-4,5,6,7-tetrahydro4,7-ethano-2H-isoindole,
  and 1,3-di-(4-fluorophenyl)-4,7-methano-4,5,6,7-tetrahydro-2H-isoindole, their isomers, and also addition salts thereof with a pharmaceutically acceptable acid or base.

Among the pharmaceutically acceptable acids there may be mentioned, without implying any limitation, hydrochloric, hydrobromic, sulphuric, phosphonic, acetic, trifluoroacetic, lactic, pyruvic, succinic, glutaric, fumaric, tartaric, maleic, citric, ascorbic, oxalic, methanesulphonic, camphoric acid, etc. . . . .

Among the pharmaceutically acceptable bases there may be mentioned, without implying any limitation, sodium hydroxide, potassium hydroxide, triethylamine, diethylamine, tert-butylamine, arginine, lysine, etc. . . .

The invention extends also to a process for the preparation of the compounds of formula (I) which is characterised in that there are used as starting material:
Either Compounds of Formula (II/a):

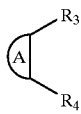

(II/a)

wherein
A is as defined for formula (I),
$R_3$ represents a cyano group and
$R_4$ represents a linear or branched $(C_1-C_6)$ alkoxycarbonyl group,
which compounds of formula (II/a) are subjected to the action of a magnesium compound of formula (III):

$R_1MgY$ (III)

wherein:
$R_1$ is as defined for formula (I),
and Y represents a halogen atom, such as bromine or chlorine,
to yield the compounds of formula (I/a), a particular case of the compounds of formula (I):

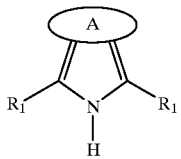

(I/a)

wherein $R_1$ and A are as defined for formula (I),
or Compounds of Formula (II/b):

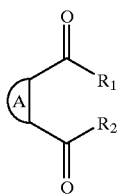

(II/b)

wherein A, $R_1$ and $R_2$ are as defined for formula (I), which are condensed:
either in the presence of an organic acid, such as acetic acid, with a compound of formula (IV):

$R-NH_2$ (IV)

wherein R is as defined for formula (I), with the proviso that R is other than a hydrogen atom, to yield the compounds of formula (I/b), a particular case of the compounds of formula (I):

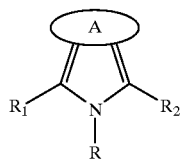

(I/b)

wherein:
$R_1$ and $R_2$, which may be identical or different, are as defined for formula (I),
A is as defined for formula (I) and R is as defined for formula (I) with the proviso that it is not a hydrogen atom,
which compounds of formula (I/b) are optionally subjected to the action of a dealkylation, deamination or deacylation agent according to the nature of the group R to yield the compounds of formula (I/c), a particular case of the compounds of formula (I):

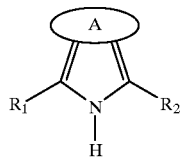

(I/c)

wherein $R_1$, $R_2$ and A are as defined hereinabove,
or with ammonium formate $HCO_2^-NH_4^+$ to yield the compounds of formula (I/c) directly, a particular case of the compounds of formula (I):

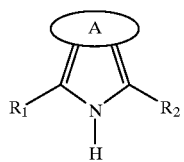

(I/c)

wherein $R_1$ and $R_2$ (identical or different), and A are as defined for formula (I),
it being possible for each of the compounds (I/a), (I/b) and (I/c) optionally to be subjected to a catalytic reduction, in the cases where the ring A comprises at least one unsaturation, to yield the compounds of formula (I/d), a particular case of the compounds of formula (I):

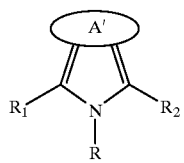

(I/d)

wherein R, $R_1$ and $R_2$ are as defined for formula (I) and A' represents an (optionally substituted) saturated, mono- or bi-cyclic $(C_3-C_{12})$-cycloalkyl group,
which compounds of formulae (I/a) to (I/d) are purified, if necessary, according to a conventional purification technique, are separated, where appropriate, into their isomers according to a conventional separation technique, and are converted, if desired, into their addition salts with a pharmaceutically acceptable acid or base.

The compounds of formulae (II), ((II/a) and (II/b)), are either commercially available compounds or are obtained, in the case of the compounds of formula (II/a), according to the conditions described by *J. Am. Chem. Soc.*, 1962, 84, 2196 and, in the case of the compounds of formula (II/b), by a Diels-Alder reaction between an unsaturated diketone and a diene.

The invention extends also to pharmaceutical compositions comprising as active ingredient at least one compound of formula (I), alone or in combination with one or more pharmacologically acceptable, inert, non-toxic excipients. Of the pharmaceutical compositions according to the invention there may be mentioned more especially those which are suitable for oral, parenteral (intravenous, intramuscular or subcutaneous), percutaneous, transcutaneous, nasal, rectal, perlingual, ocular or respiratory administration, and especially tablets, dragees, sublingual tablets, soft gelatin capsules, hard gelatin capsules, suppositories, creams, ointments, dermal gels, injectable or drinkable preparations, eye or nose drops etc. . . .

The invention also includes, for their use as medicaments, the following compounds, which are particular cases of the compounds of formula (I), wherein:

when $R_1$ and $R_2$ are identical and each represents a phenyl group and R represents a hydrogen atom, then A, together with the atoms in common with the pyrrole ring, represents a cyclohexane, and when $R_1$ and $R_2$ are identical and each represents a phenyl group and R represents a hydrogen atom, then A, together with the atoms in common with the pyrrole ring, represents a norbornene, and when $R_1$ represents a phenyl group, $R_2$ represents a 1-isoquinolyl group and R represents a hydrogen atom, then A, together with the atoms in common with the pyrrole ring, represents a cyclohexane, and when $R_1$ represents a phenyl group $R_2$ represents a para-nitrophenyl group and R represents a hydrogen atom, then A, together with the atoms in common with the pyrrole ring, represents a norbornane.

The invention extends similarly to pharmaceutical compositions comprising as active ingredient at least one compound corresponding to one of those four structures, which are particular cases of the compounds of formula (I) as defined hereinabove, alone or in combination with one or more pharmacologically acceptable, inert, non-toxic excipients, for use as inhibitors of cyclooxygenase-2, interleukin 1β and inducible nitric oxide synthase.

The dosage used is adaptable according to the nature and severity of the disorder, the use of any associated treatments, the administration route and the age and weight of the patient. That dosage ranges from 0.1 mg to 1 g in one or more administrations per day.

The following Examples illustrate the invention but do not limit it in any way.

The starting materials used are known products or are products prepared according to known procedures. The different Steps result in synthesis intermediates for use in the preparation of the compounds of the invention.

The structures of the compounds described in the Examples were determined according to conventional spectrophotometric techniques (infra-red, nuclear magnetic resonance, mass spectrometry . . . ).

PREPARATION

The products of the various preparations, for use as starting materials in the synthesis of the compounds of the invention described in the various Examples, were obtained by reaction between a diene and a dienophile according to the operating conditions described, for example, in *J. Am. Chem. Soc.*, 1940, 62, 56–61.

PREPARATION 1: 1,2-dimethyl-4,5-dibenzoylcyclohexene

The product is obtained by reaction between the diene, 2,3-dimethyl-1,3-butadiene, and a dienophile, 1,4-diphenyl-2-butene-1,4-dione.

PREPARATION 2: 4,5-dibenzoylcyclohexene

The product is obtained by reaction between the diene, 1,3-butadiene and the dienophile of Preparation 1.

PREPARATION 3: 5,6-dibenzoylbicyclo[2.2.1]hept-2-ene

The product is obtained by reaction between the diene, cyclopentadiene and the dienophile of Preparation 1.

PREPARATION 4: 5,6-dibenzoylbicyclo[2.2.2]oct-2-ene

The product is obtained by reaction between the diene, 1,3-cyclohexadiene and the dienophile of Preparation 1.

PREPARATION 5: 5,6-(4-fluorobenzoyl)-bicyclo[2.2.1]hept-2-ene

The product is obtained by reaction between the diene of Preparation 3 and a dienophile, 1,4-di-(4-fluorophenyl)-2-butene-1,4-dione.

PREPARATION 6: 4,5-di-(4-methoxybenzoyl)-cyclohexene

The product is obtained by reaction between 1,3-butadiene and 1,4-di-(4-methoxyphenyl)-2-butene-1,4-dione.

PREPARATION 7: 4,5-di-(4-chlorobenzoyl)-cyclohexene

The product is obtained by reaction between the diene of Preparation 6 and 1,4-di-(4-chlorophenyl)-2-butene-1,4-dione.

PREPARATION 8: 2-(4-fluorobenzoyl)-3-[(4-methylsulphonyl)benzoyl]-bicyclo[2.2.1]-heptane The product of Preparation 5 is treated under the conditions of Example 9, then placed in the presence of sodium thiomethanolate in dimethyl sulphoxide according to conventional operating conditions. The product obtained is then subjected to oxydation to allow isolation of the expected product.

PREPARATION 9: 2,3-di-[(4-methylsulphonyl)benzoyl]-bicyclo[2.2.1]heptane

The product is obtained as co-product in the synthesis of the compound of Preparation 8.

PREPARATION 10: 4,5-di-[4-(1H-imidazolyl)benzoyl]cyclohexene

The product is obtained by reaction between the diene of Preparation 6 and 1,4-di-(4-fluorophenyl)-2-butene-1,4-dione, followed by treatment with imidazole in the presence of potassium hydroxide, in dimethyl sulphoxide.

PREPARATION 11: 5,6-di-(4-pyridylcarbonyl)-bicyclo[2.2.1]hept-2-ene

The product is obtained by reaction between cyclopentadiene and 1,4-di-(4-pyridyl)-2-butene-1,4-dione.

PREPARATION 12: 5,6-di-(2,4-difluorobenzoyl)-bicyclo[2.2.1]hept-2-ene

The product is obtained by reaction between cyclopentadiene and 1,4-di-(2,4-difluorophenyl)-2-butene-1,4-dione.

PREPARATION 13: 5,6-di-(3,4-difluorobenzoyl)-bicyclo[2.2.1]hept-2-ene

The product is obtained by reaction between cyclopentadiene and 1,4-di-(3,4-difluorophenyl)-2-butene-1,4-dione.

PREPARATION 14: 5,6-di-[(5-fluoro)-2-pyridylcarbonyl]-bicyclo[2.2.1]hept-2-ene

The product is obtained by reaction between cyclopentadiene and 1,4-di-[(5-fluoro)-2-pyridyl]-2-butene-1,4-dione.

PREPARATION 15: 5,6-di-[(6-fluoro)-3-pytidylcarbonyl]-bicyclo[2.2.1]hept-2-ene

The product is obtained by reaction between cyclopentadiene and 1,4-di-[(6-fluoro)-3-pyridyl]-2-butene-1,4-dione.

PREPARATION 16: 5,6-di-(2-furylcarbonyl)-bicyclo[2.2.1]hept-2-ene

The product is obtained by reaction between cyclopentadiene and 1,4-di-(2-furyl)-2-butene-1,4-dione.

PREPARATION 17: 5,6-di-(2-thienylcarbonyl)-bicyclo[2.2.1]hept-2-ene

The product is obtained by reaction between cyclopentadiene and 1,4-di-(2-thienyl)-2-butene-1,4-dione.

PREPARATION 18: 5,6-di-[(4-fluoro)-2-nitrobenzoyl]-bicyclo[2.2.1]hept-2-ene

The product is obtained by reaction between cyclopentadiene and 1,4-di-[(4-fluoro)-2-nitrophenyl]-2-butene-1,4-dione.

PREPARATION 19: 5,6-di-[(4-fluoro)-3-nitrobenzoyl]-bicyclo[2.2.1]-hept-2-ene

The product is obtained by reaction between cyclopentadiene and 1,4-di-[(4-fluoro)-3-nitrophenyl]-2-butene-1,4-dione.

PREPARATION 20: 5,6-di-(4-fluorobenzoyl)-bicyclo[2.2.2]oct-2-ene

The product is obtained by reaction between 1,3-cyclohexadiene and the dienophile used in Preparation 5.

PREPARATION 21: 5,6di-[(4-fluoro)benzoyl]-oxo-7-bicyclo[2.2.1]hept-2-ene

The product is obtained by reaction between a diene, furan and the dienophile used in Preparation 5.

EXAMPLE 1

1,3-di-(4-fluorophenyl)-4,5,6,7-tetrahydro-2H-isoindole

Step A: tert-butyl cis-2-cyanocyclohexanecarboxylate 46.25 g of cis-cyclohexane-1,2-dicarboxylic anhydride are slowly added, at a temperature below 25° C., to a solution of 66 ml of 10N ammoniac. After 18 hours the solution is acidified by the addition of 12N hydrochloric acid, causing the formation of a precipitate which is filtered off, washed with water and dried. The 51 g of cis-2-carboxamidocyclohexanecarboxylic acid so obtained are mixed with 180 ml of pyridine and 75 ml of tert-butanol. 115 ml of benzenesulphonyl chloride are then added dropwise while maintaining the temperature at approximately 40° C. After reaction for 12 hours at ambient temperature the solution is hydrolysed by the addition of 600 ml of water and then extracted with ethyl ether. After washing, the organic phases are dried over calcium sulphate and concentrated. The residue is distilled and 55.7 g of the expected product are obtained.

Step B: 1,3-di-(4-fluorophenyl)-4,5,6,7-tetrahydro-2H-isoindole

A solution of 14.75 g of the compound of Step A diluted with 30 ml of ethyl ether is added dropwise, at 35° C., to 80 ml of a 2M solution of 4-fluorophenylmagnesium bromide in ethyl ether. After 2 hours, the reaction mixture is cooled and hydrolysed with 20 ml of a saturated ammonium chloride solution. After filtration and washing with ethyl ether, the organic phases are combined and dried over calcium sulphate and then concentrated. The product is isolated by chromatography on silica gel (eluant: cyclohexane/ethyl acetate: 97.5/2.5). Crystallisation yields 2 g of the product.

Elemental Microanalysis:

|  | C | H | N |
|---|---|---|---|
| % calculated | 77.66 | 5.54 | 4.53 |
| % found | 77.26 | 5.52 | 4.42 |

EXAMPLE 2

1,3-diphenyl-4,5,6,7-tetrahydro-2H-isoindole

The expected product is obtained in accordance with the process described in Example 1, using phenylmagnesium bromide as the reagent in Step B.

Elemental Microanalysis:

|  | C | H | N |
|---|---|---|---|
| % calculated | 87.87 | 7.00 | 5.12 |
| % found | 87.87 | 7.28 | 5.37 |

Melting Point: 146° C.

EXAMPLE 3

1,3-di(4-methylthiophenyl)-4,5,6,7-tetrahydro-2H-isoindole

The expected product is obtained in accordance with the process described in Example 1, using 4-methylthiophenylmagnesium bromide as the reagent in Step B.

Elemental Microanalysis:

|  | C | H | N | S |
|---|---|---|---|---|
| % calculated | 72.28 | 6.34 | 3.83 | 17.54 |
| % found | 72.11 | 6.40 | 4.07 | 17.40 |

Melting Point: 174° C.

EXAMPLE 4

1,3-diphenyl-2,4,5,6-tetrahydrocyclopenta[c]pyrrole

Step A: tert-butyl cis-2-cyanocyclopentanecarboxylate

The procedure is as in Step A of Example 1, using cis-cyclopentane-1,2-dicarboxylic anhydride as substrate.

Step B: 1,3-diphenyl-2,4,5,6-tetrahydrocyclopenta[c]pyrrole

The expected product is obtained by reacting the compound of Step A with the reagent used in Example 2 in accordance with the conditions of Step B of Example 1.

Elemental Microanalysis:

|  | C | H | N |
|---|---|---|---|
| % calculated | 87.99 | 6.61 | 5.40 |
| % found | 88.12 | 6.70 | 5.38 |

Melting Point: 190° C.

EXAMPLE 5

1,3-diphenyl-4,7-dihydro-2H-isoindole

Step A: tert-butyl cis-2-cyano-4,5-cyclohexenecarboxylate

The procedure is as in Step A of Example 1, using cis4,5-cyclohexene-1,2-dicarboxylic anhydride as substrate.

Step B: 1,3diphenyl-4,7dihydro-2H-isoindole

The expected product is obtained by reacting the compound of Step A with the reagent used in Example 2 in accordance with the conditions of Step B of Example 1.

Elemental Microanalysis:

|  | C | H | N |
|---|---|---|---|
| % calculated | 88.44 | 6.18 | 5.15 |
| % found | 88.52 | 6.31 | 5.16 |

Melting Point: 138° C.

EXAMPLE 6

1,3-diphenyl-5,6-dimethyl-4,7-dihydro-2H-isoindole

A solution containing 4.46 g of 1,2-dimethyl-4,5-dibenzoylcyclohexene (Preparation 1) and 8.81 g of ammonium formate in 70 ml of anhydrous ethanol is heated at reflux for 24 hours. A precipitate is obtained which is filtered off and then dissolved in dichloromethane. The organic phase is washed with water, dried over calcium sulphate and concentrated to allow the isolation of 4 g of the expected product.

Elemental Microanalysis:

|  | C | H | N |
|---|---|---|---|
| % calculated | 88.25 | 7.07 | 4.60 |
| % found | 87.81 | 7.04 | 4.45 |

Melting Point: 212° C.

EXAMPLE 7

1,3-diphenyl-2,5,6-trimethyl-4,7-dihydro-2H-isoindole

The procedure is as in Example 6, using as the reagent 10 equivalents of an aqueous 40% methylamine solution in the presence of 5 equivalents of acetic acid.

Elemental Microanalysis:

|  | C | H | N |
|---|---|---|---|
| % calculated | 88.14 | 7.40 | 4.47 |
| % found | 88.30 | 7.40 | 4.54 |

Melting Point: 200–201° C.

EXAMPLE 8

1,3-diphenyl-2-benzyloxycarbonylamino-4,7-dihydro-2H-isoindole

The procedure is as in Example 6, using as the reagents 5 equivalents of benzyloxycarbonylhydrazine and 5 equivalents of acetic acid.

Elemental Microanalysis:

|  | C | H | N |
|---|---|---|---|
| % calculated | 79.98 | 5.75 | 6.66 |
| % found | 79.62 | 5.86 | 6.56 |

Melting Point: 184° C.

EXAMPLE 9

1,3-diphenyl-5,6-dimethyl-4,5,6,7-tetrahydro-2H-isoindole 1 g of the product obtained in Example 6, 1.2 g of ammonium format and 0.2 g of 10% Pd/C in 70 ml of ethanol are heated at reflux for 3 hours, then filtered and concentrated. The expected product is isolated by chromatography on silica gel (eluant: cyclohexane/ethyl acetate: 90/10).

Elemental Microanalysis:

|  | C | H | N |
|---|---|---|---|
| % calculated | 87.66 | 7.69 | 4.65 |
| % found | 87.44 | 7.57 | 4.45 |

Melting Point: 133° C.

EXAMPLE 10

1,3-diphenyl-2-methyl-4,5,6,7-tetrahydro-2H-isoindole

Step A: 1,3-diphenyl-2-methyl-4,7-dihydro-2H-isoindole

The procedure is as in Example 7, using as substrate 4,5-dibenzoylcyclohexene (Preparation 2).

Step B: 1,3-diphenyl-2-methyl-4,5,6,7-tetrahydro-2H-isoindole

The procedure is as in Example 9, using as substrate the product of Step A.

Elemental Microanalysis:

|  | C | H | N |
|---|---|---|---|
| % calculated | 87.76 | 7.36 | 4.87 |
| % found | 87.6 | 7.22 | 4.88 |

Melting Point: 143° C.

EXAMPLE 11

1,3-diphenyl-4,5,6,7-tetrahydro-2H-2-isoindolamine

The procedure is as in Example 9, using as substrate the product of Example 8.

Elemental Microanalysis:

|  | C | H | N |
|---|---|---|---|
| % calculated | 83.30 | 6.99 | 9.71 |
| % found | 83.34 | 7.01 | 9.58 |

Melting Point: 161° C.

EXAMPLE 12

1-phenyl-3-(4-methylthiophenyl)-4,5,6,7-tetrahydro-2H-isoindole

Step A: 1-phenyl-3-(4-methylthiophenyl)-4,7-dihydro-2H-isoindole

The procedure is as in Example 6, using as starting material 4-benzoyl-5-(4-methylthio)-benzoylcyclohexene.

Step B: 1-phenyl-3-(4-methylthiophenyl)-4,5,6,7-tetrahydro-2H-isoindole

The procedure is as in Example 9, using the product obtained in Step A.

Elemental Microanalysis:

|  | C | H | N | S |
|---|---|---|---|---|
| % calculated | 78.95 | 6.63 | 4.38 | 10.04 |
| % found | 78.91 | 6.61 | 4.39 | 9.96 |

Melting Point: 150° C.

EXAMPLE 13

1,3-diphenyl-4,7-methano-4,5,6,7-tetrahydro-2H-isoindole

Step A: 1,3-iphenyl-4,7-dihydro-4,7-methano-2H-isoindole

The procedure is as in Example 6, using as substrate the product of Preparation 3.

Step B: 1,3-diphenyl-4,7-methano-4,5,6,7-tetrahydro-2H-isoindole

The procedure is as in Example 9, using the product of Step A.

Elemental Microanalysis:

|  | C | H | N |
|---|---|---|---|
| % calculated | 88.38 | 6.71 | 4.91 |
| % found | 88.44 | 6.96 | 4.73 |

Melting Point: 162° C.

EXAMPLE 14

1,3-diphenyl-2-dimethanesulphonylamino-4,5,6,7-tetrahydro-2H-isoindole 1,3-Diphenyl-4,5,6,7-tetrahydro-2H-2-isoindolamine (Example 11) is treated with 2 equivalents of methanesulphonyl chloride.

Elemental Microanalysis:

|  | C | H | N | S |
|---|---|---|---|---|
| % calculated | 59.44 | 5.44 | 6.30 | 14.42 |
| % found | 59.83 | 5.77 | 6.31 | 14.13 |

Melting Point: >250° C. (decomposition).

EXAMPLE 15

1,3-di-(4-fluorophenyl)-2,4,5,6-tetrahydrocyclopenta[c]pyrrole

The expected product is obtained by reacting tert-butyl cis-2-cyanocyclopentanecarboxylate (Example 4, Step A) in accordance with the conditions of Step B of Example 1.

Elemental Microanalysis:

|  | C | H | N |
|---|---|---|---|
| % calculated | 77.27 | 5.12 | 4.74 |
| % found | 77.55 | 4.87 | 4.71 |

Melting Point: 170° C.

EXAMPLE 16

1,3-di(4-methylphenyl)-4,5,6,7-tetrahydro-2H-isoindole

The expected product is obtained in accordance with the process described in Example 1, using 4-methylphenylmagnesium bromide as the reagent in Step B.

Elemental Microanalysis:

|  | C | H | N |
|---|---|---|---|
| % calculated | 87.66 | 7.69 | 4.65 |
| % found | 87.78 | 8.02 | 4.76 |

Melting Point: 150° C.

EXAMPLE 17

1,3-diphenyl-4,7-dihydro-4,7-ethano-2H-isoindole

The expected product is obtained by reacting the compound of Preparation 4 in accordance with the conditions of Example 6.

Elemental Microanalysis:

|  | C | H | N |
|---|---|---|---|
| % calculated | 88.85 | 6.44 | 4.71 |
| % found | 88.36 | 6.50 | 4.72 |

Melting Point: 224° C.

EXAMPLE 18

1,3-diphenyl-4,5,6,7-tetrahydro-4,7-ethano-2H-isoindole

The expected product is obtained by reacting the compound of Example 17 in accordance with the conditions of Example 9.

Elemental Microanalysis:

|  | C | H | N |
|---|---|---|---|
| % calculated | 88.25 | 7.07 | 4.68 |
| % found | 88.10 | 7.29 | 4.62 |

Melting Point: 248° C.

EXAMPLE 19

1,3-di-(4-fluorophenyl)-4,7-methano-4,5,6,7-tetrahydro-2H-isoindole

Step A: 1,3-di-(4-fluorophenyl)-4,7-dihydro-4,7-methano-2H-isoindole

The procedure is in accordance with Example 6, using as substrate the product of Preparation 5.

Step B: 1,3-di-(4-fluorophenyl)-4,7-methano-4,5,6,7tetrahydro-2H-isoindole

The product obtained in Step A is treated under the conditions of Example 9, replacing the ammonium formate with cyclohexene.

Elemental Microanalysis:

|  | C | H | N |
|---|---|---|---|
| % calculated | 78.49 | 5.33 | 4.36 |
| % found | 78.59 | 5.36 | 4.40 |

Melting Point: 146° C.

EXAMPLE 20

1,3-di-(4-methoxyphenyl)-4,5,6,7-tetrahydro-2H-isoindole

Step A: 1,3-di-(4-methoxyphenyl)-4,7-dihydro-2H-isoindole

The procedure is as in Example 6, using as substrate 4,5-di-(4-methoxybenzoyl)cyclohexene (Preparation 6).

Step B: 1,3-di-(4-methoxyphenyl)-4,5,6,7-tetrahydro-2H-isoindole

The procedure is as in Example 9, using the product of Step A.

Elemental Microanalysis:

|  | C | H | N |
|---|---|---|---|
| % calculated | 79.25 | 6.95 | 4.20 |
| % found | 78.65 | 6.83 | 4.28 |

Melting Point: 146° C.

EXAMPLE 21

1,3-di-(4-chlorophenyl)-4,5,6,7-tetrahydro-2H-isoindole

Step A: 1,3-di-(4-chlorophenyl)-4,7-dihydro-2H-isoindole

The procedure is as in Example 6, using as substrate 4,5-di-(4-chlorobenzoyl)cyclohexene (Preparation 7).

Step B: 1,3-di-(4-chlorophenyl)-4,5,6,7-tetrahydro-2H-isoindole

The procedure is as in Example 19, using the product of Step A.

Elemental Microanalysis:

|  | C | H | N | Cl |
|---|---|---|---|---|
| % calculated | 70.19 | 5.01 | 4.09 | 20.72 |
| % found | 70.03 | 5.07 | 4.20 | 20.22 |

Melting Point: 231° C.

EXAMPLE 22

1,3-diphenyl-2-carboxymethyl-4,5,6,7-tetrahydro-2H-isoindole

Step A: 1,3-diphenyl-2-tert-butoxycarbonylmethyl-4,7-dihydro-2H-isoindole

The procedure is as in Example 6, using as substrate 4,5-dibenzoylcyclohexene (Preparation 2) and as the reagent tert-butyl 2-aminoacetate in the presence of acetic acid.

Step B: 1,3-diphenyl-2-carboxymethyl-4,7-dihydro-2H-isoindole 5 ml of trifluoroacetic acid are added at 0° C. to a solution of 5 g of the compound of Step A in 50 ml of anhydrous dichloromethane. After reaction for 12 hours at ambient temperature, the reaction mixture is concentrated in vacuo and the residue obtained is rinsed with ether to allow isolation of the expected product.

Step C: 1,3-diphenyl-2-carboxymethyl-4,5,6,7-tetrahydro-2H-isoindole

The procedure is as in Example 9, using the product of Step B.

Elemental Microanalysis:

|  | C | H | N |
|---|---|---|---|
| % calculated | 79.73 | 6.39 | 4.23 |
| % found | 79.72 | 6.58 | 4.19 |

Melting Point: 162° C.

EXAMPLE 23

(d,l)-1-(4-fluorophenyl)-3-[(4-methylsulphonyl)phenyl]-4,7-methano-4,5,6,7-tetrahydro-2H-isoindole The procedure is as in Example 6, using as substrate the product of Preparation 8.

Elemental Microanalysis:

|  | C | H | N | S |
|---|---|---|---|---|
| % calculated | 69.27 | 5.28 | 3.67 | 8.41 |
| % found | 69.16 | 5.59 | 3.56 | 7.94 |

Melting Point: >260° C.

EXAMPLE 24

2-benzyl-4,6-diphenyl-1,2,3,5-tetrahydropyrrolo[3,4-c]pyrrole

The procedure is as in Example 6, using as substrate 3,4-dibenzoyl-1-benzyl-2,3,4,5-tetrahydro-1H-pyrrole;

Elemental Microanalysis:

|  | C | H | N |
|---|---|---|---|
| % calculated | 85.68 | 6.33 | 7.99 |
| % found | 85.53 | 6.46 | 7.97 |

Melting Point: 182° C.

EXAMPLE 25

1,3-di[(4-methylsulphonyl)phenyl]-4,7-methano-4,5,6,7-tetrahydro-2H-isoindole

The procedure is as in Example 6, using as substrate the product of Preparation 9.

Elemental Microanalysis:

|  | C | H | N | S |
|---|---|---|---|---|
| % calculated | 62.56 | 5.25 | 3.17 | 14.52 |
| % found | 61.93 | 5.64 | 3.17 | 14.14 |

Melting Point: >260° C.

EXAMPLE 26

1,3-di-[4-(1H-imidazolyl)phenyl]-4,5,6,7-tetrahydro-2H-isoindole dihydrochloride Step A: 1,3-di-[4-(1H-imidazolyl)phenyl]-4,7-dihydro-2H-isoindole The procedure is as in Example 6, using as substrate the product of Preparation 10.

Step B: 1,3-di-[4-(1H-imidazolyl)phenyl]-4,5,6,7-tetrahydro-2H-isoindole dihydrochloride The procedure is as in Example 9, using the product of Step A.

Elemental Microanalysis:

|  | C | H | N | Cl |
|---|---|---|---|---|
| % calculated | 65.27 | 5.27 | 14.64 | 14.82 |
| % found | 65.38 | 5.59 | 14.71 | 15.30 |

Melting Point: >260° C.

EXAMPLE 27

1,3-diphenyl-2H-pyrrolidine[3,4-c]pyrrole hydrochloride

The procedure is as in Example 9, using as substrate the product obtained in Example 24.

Melting Point: >260° C.

EXAMPLE 28

1-(4-fluorophenyl)-3-[4-(1H-imidazolyl)phenyl]-4,5,6,7-tetrahydro-2H-isoindole

The procedure is as in Example 6, using as substrate 2-(4-fluorobenzoyl)-1-[4-(1H-imidazolyl)benzoyl]cyclohexane.

Elemental Microanalysis:

|  | C | H | N |
|---|---|---|---|
| % calculated | 77.29 | 5.64 | 11.76 |
| % found | 76.76 | 5.72 | 11.72 |

Melting Point: >250° C.

EXAMPLE 29

1,3-di-(4-fluorophenyl)-4,7-dihydro-4,7-methano-2H-isoindole

The procedure is as in Example 19, stopping after Step A.

Elemental Microanalysis:

|  | C | H | N |
|---|---|---|---|
| % calculated | 78.98 | 4.73 | 4.39 |
| % found | 79.30 | 4.76 | 4.42 |

Melting Point: 189° C.

EXAMPLE 30

1,3-diphenyl-2-methanesulphonylamino-4,5,6,7-tetrahydro-2H-isoindole

The procedure is as in Example 14, using the same substrate but only one equivalent of methanesulphonyl chloride as reagent.

Elemental Microanalysis:

|  | C | H | N | S |
|---|---|---|---|---|
| % calculated | 68.83 | 6.05 | 7.64 | 8.75 |
| % found | 68.94 | 6.32 | 7.63 | 9.07 |

Melting Point: 196° C.

EXAMPLE 31

1,3-di-(4-pyridyl)-4,7-methano-4,5,6,7-tetrahydro-2H-isoindole dihydrochloride

The procedure is as in Example 19, Steps A and B, using as substrate in Step A the product of Preparation 11.

Elemental Microanalysis:

|  | C | H | N | Cl |
|---|---|---|---|---|
| % calculated | 63.34 | 5.32 | 11.66 | 19.68 |
| % found | 63.69 | 5.67 | 11.73 | 19.44 |

Melting Point: 264° C.

EXAMPLE 32

1,3-di-(2,4-difluorophenyl)-4,7-methano-4,5,6,7-tetrahydro-2H-isoindole

The procedure is as in Example 19, Steps A and B, using as substrate in Step A the product of Preparation 12.

EXAMPLE 33

1,3-di-(3,4-difluorophenyl)-4,7-methano-4,5,6,7-tetrahydro-2H-isoindole

The procedure is as in Example 19, Steps A and B, using as substrate in Step A the product of Preparation 13.

EXAMPLE 34

1,3-di-(5-fluoro-2-pyridyl)-4,7-methano-4,5,6,7-tetrahydro-2H-isoindole

The procedure is as in Example 19, Steps A and B, using as substrate in Step A the product of Preparation 14.

EXAMPLE 35

1,3-di-(6-fluoro-3-pyridyl)-4,7-methano-4,5,6,7-tetrahydro-2H-isoindole

The procedure is as in Example 19, Steps A and B, using as substrate in Step A the product of Preparation 15.

EXAMPLE 36

1,3-di-(2-furyl)-4,7-methano-4,5,6,7-tetrahydro-2H-isoindole

The procedure is as in Example 19, Steps A and B, using as substrate in Step A the product of Preparation 16.

EXAMPLE 37

1,3-di-(2-thienyl)-4,7-methano-4,5,6,7-tetrahydro-2H-isoindole

The procedure is as in Example 19, Steps A and B, using as substrate in Step A the product of Preparation 17.

EXAMPLE 38

1,3-di-(2-amino-4-fluorophenyl)-4,7-methano-4,5,6,7-tetrahydro-2H-isoindole

Step A: 1,3-di-(4-fluoro-2-nitrophenyl)-4,7-methano-4,5,6,7-tetrahydro-2H-isoindole The procedure is as in Example 19 Steps A and B, using as substrate in Step A the product of Preparation 18.

Step B: 1,3-di-(2-amino-4-fluorophenyl)-4,7-methano-4,5,6,7-tetrahydro-2H-isoindole A solution containing 1 equivalent of the compound obtained in Step A in 30 ml of methanol and 100 mg of 10% palladium on carbon is heated for 2 hours at 40° C. After returning to ambient temperature, the reaction mixture is filtered over Celite and then concentrated under reduced pressure to allow isolation of the expected product.

EXAMPLE 39

1,3-di-(4-fluoro-2-(N-methyl)aminophenyl)-4,7-methano-4,5,6,7-tetrahydro-2H-isoindole A solution containing 1 equivalent of the compound obtained in Example 38 is reacted at ambient temperature in formaldehyde in the presence of formic acid in accordance with the conditions described in Org. React., 1949, 5, 290 to allow isolation of the expected product.

EXAMPLE 40

1,3-di-(4-fluoro-2-dimethylaminophenyl)-4,7-methano-4,5,6,7-tetrahydro-2H-isoindole A solution containing 1 equivalent of the compound obtained in Example 38, 2.2 equivalents of methyl iodide and 2 equivalents of $K_2CO_3$ in 40 ml of dimethylformamide is stirred for 12 hours at ambient temperature. After concentration at reduced pressure the residue is diluted with dichloromethane and then the organic phase is washed with a saturated NaCl solution. After drying over sodium sulphate and concentration under reduced pressure, chromatography on silica gel allows isolation of the expected product.

EXAMPLE 41

1,3-di-(3-amino-4-fluorophenyl)-4,7-methano-4,5,6,7-tetrahydro-2H-isoindole

The procedure is as in Example 38, Steps A and B, using as substrate in Step A the product obtained in Preparation 19.

EXAMPLE 42

1,3-di-(4-fluoro-3-(N-methyl)aminophenyl)-4,7-methano-4,5,6,7-2H-isoindole

The procedure is as in Example 39, using as substrate the product obtained in Example 41.

Melting Point: 196° C.

EXAMPLE 43

1,3-di-(4-fluoro-3-dimethylaminophenyl)-4,7-methano-4,5,6,7-tetrahydro-2H-isoindole The procedure is as in Example 40, using as substrate the product obtained in Example 41.

EXAMPLE 44

1,3-di-(4-fluorophenyl)-4,5,6,7-tetrahydro-4,7-ethano-2H-isoindole

The expected product is obtained by reacting the compound of Preparation 20 in accordance with the conditions of Example 6, then in accordance with the conditions of Example 9.

EXAMPLE 45

1,3-di-(3-acetamido-4-fluorophenyl)-4,7-methano-4,5,6,7-tetrahydro-2H-isoindole

The expected product is obtained by reacting the compound of Example 41 under conventional acylation conditions.

Melting Point: 225° C.

EXAMPLE 46

5,7-di-(4-fluorophenyl)-1,2,3,4-tetrahydro-1,4-epoxy-6H-isoindole

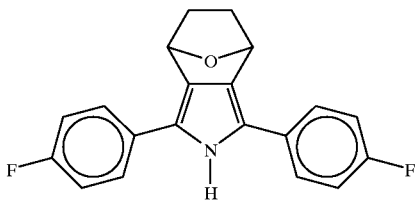

The procedure is as in Example 19, Steps A and B, using as substrate in Step A the product of Preparation 21.

PHARMACOLOGICAL STUDY OF THE COMPOUNDS OF THE INVENTION

EXAMPLE 47

Biological Activity of the Compounds on Cyclooxygenase 1 and 2

The inhibitory activities of the compounds in relation to COX 1 and COX 2 were evaluated using mice peritoneal macrophages exposed to inflammatory stimuli (zymosan and LPS, respectively) in accordance with the method described by Tordjman et al., *Biochimica et Biophysica Acta*, 1995, 1256, 249–56.

The results are given in Table 1:

TABLE 1

| Example | IC$_{50}$ ($\mu$M) | |
|---|---|---|
| | cox 1 | cox 2 |
| 1 | 0.1–0.5 | 0.001 |
| 2 | 0.1–0.5 | 0.001 |
| 4 | 0.1–0.5 | 0.0005–0.001 |
| 5 | 0.1 | 0.001–0.01 |
| 19 | 0.1 | 0.001 |

The compounds also inhibit the production of IL1β by THP1 line cells stimulated with LPS. For example, the compound of Example 9 has an IC$_{50}$ of the order of 1 $\mu$M in that model. In addition, those compounds exert an activity in animals especially by inhibiting the production of prostaglandins in the carrageenin air-pouch model in the mouse (Whittle, B. J. R. et al., *Nature*, 1980, 284, 271–273; Masferrer, J. L. et al., *Proc. Natl. Acad. Sci. USA*, 1994, 91, 3228–3232). Thus, in that model, the compound of Example 19 exhibits a powerful activity having an oral ED$_{50}$ of 2.5 mg/kg. Gastric tolerance, evaluated in the mouse after fasting for 24 hours and 5 hours after oral treatment, has proved excellent for all of the compounds: absence of macroscopic effects up to a dose of 800 mg/kg. In addition, the present compounds inhibited the NO production in mouse peritoneal macrophages stimulated with LPS. For example, the compound of Example 19 exhibited a concentration-related inhibition with an IC$_{50}$ value of 2,5 $\mu$M.

EXAMPLE 48

Formulation for the Preparation of 1000 Tablets each Comprising 10 mg of Active Ingredient

| | |
|---|---|
| 1,3-di(4-fluorophenyl)-4,7-methano-4,5,6,7-tetrahydro-2H-isoindole | 10 g |
| wheat starch | 10 g |
| lactose | 100 g |
| magnesium stearate | 3 g |
| silica | 2 g |
| hydroxypropyl cellulose | 2 g |

What is claimed is:
1. A compound selected from those of formula (I):

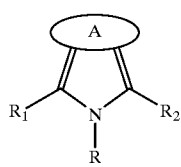

(I)

in which:
R represents:
hydrogen,
a linear or branched (C$_1$–C$_6$)-alkyl optionally substituted by one or more identical or different groups selected from hydroxy, linear or branched (C$_1$–C$_6$)-alkoxy, carboxy, and linear or branched (C$_1$–C$_6$)-alkoxycarbonyl,
an amino optionally substituted by one or two identical or different groups selected from linear or branched (C$_1$–C$_6$)-alkyl, linear or branched (C$_1$–C$_6$)-alkoxycarbonyl, linear or branched aryl-(C$_1$–C$_6$)-alkoxycarbonyl, linear or branched (C$_1$–C$_6$)-alkylsulphonyl, and arylsulphonyl,
or a linear or branched (C$_1$–C$_6$)-acyl,
R$_1$ and R$_2$, which may be identical or different, each represents aryl, pyridyl, or (C$_3$–C$_7$)-cycloalkyl, at least one of R$_1$ and R$_2$ being a pyridyl group, or one of those R$_1$ or R$_2$ groups which is substituted by one or more identical or different groups selected from:
halogen,
linear or branched (C$_1$–C$_6$)-alkyl optionally substituted by one or more identical or different substituents selected from halogen, hydroxy, linear or branched (C$_1$–C$_6$)-alkoxy, amino, and linear or branched (C$_1$–C$_6$)-alkoxycarbonyl,
linear or branched (C$_1$–C$_6$)-alkoxy optionally substituted by amino which is itself optionally substituted by one or two identical or different linear or branched (C$_1$–C$_6$)-alkyl,
linear or branched (C$_1$–C$_6$)-trihaloalkoxy,
linear or branched (C$_1$–C$_6$)-acyl,
hydroxy, nitro, cyano, mercapto, or carboxy,
amino optionally substituted by one or two identical or different groups selected from linear or branched (C$_1$–C$_6$)-alkyl, linear or branched (C$_1$–C$_6$)-alkylcarbonyl, and linear or branched (C$_1$–C$_6$)-alkylsulphonyl,
linear or branched (C$_1$–C$_6$)-alkoxycarbonyl,
linear or branched (C$_1$–C$_6$)-alkylthio,
sulphonyl substituted by linear or branched (C$_1$–C$_6$)-alkyl or by amino which is optionally substituted by one or two identical or different linear or branched (C$_1$–C$_6$)-alkyl, and
pyridyl optionally substituted by one or more identical or different groups selected from halogen, linear or branched (C$_1$–C$_6$)-alkyl, and linear or branched (C$_1$–C$_6$)-alkoxy,
A represents, together with the atoms in common with the pyrrole:
a saturated or mono-unsaturated monocyclic or bicyclic (C$_3$–C$_{12}$)-cycloalkyl,
a saturated heterocycle having 5 to 7 ring members and containing one or two nitrogen,
or 7-oxabicyclo[2.2.1]heptane,
or one of the said A groups which is substituted by one or more identical or different groups selected from:
halogen,
trihalomethyl,
linear or branched (C$_1$–C$_6$)-alkyl optionally substituted by one or more halogen or hydroxy groups,
linear or branched (C$_1$–C$_6$)-alkoxy,
linear or branched (C$_1$–C$_6$)-aminoalkyl,
cyano,
aryl or linear or branched aryl-(C$_1$–C$_6$)-alkyl, the aryl of the said groups being optionally substituted by one or more identical or different groups selected from halogen, hydroxy, linear or branched (C$_1$–C$_6$)-alkyl, and linear or branched (C$_1$–C$_6$)-alkoxy,
and sulphonyl substituted by linear or branched (C$_1$–C$_6$)-alkyl or by amino which is itself optionally substituted by one or two identical or different linear or branched (C$_1$–C$_6$)-alkyl,
their isomers, and also addition salts thereof with a pharmaceutically-acceptable acid or base,
provided that:

if $R_2$ represents 4-pyridyl optionally substituted by one or more groups selected from halogen, linear or branched $(C_1-C_6)$-alkyl (itself optionally substituted by hydroxy or linear or branched $(C_1-C_6)$-alkoxy), hydroxy, nitro, amino, linear or branched $(C_1-C_6)$-acyl, and linear or branched $(C_1-C_6)$-alkoxycarbonyl, and $R_1$ represents phenyl, naphthyl, or pyridyl, each of those groups being optionally substituted by one or two groups selected from halogen, linear or branched $(C_1-C_4)$-alkyl optionally substituted by halogen, linear or branched $(C_1-C_4)$-alkoxy, nitro, hydroxy, amino optionally substituted by one or two linear or branched $(C_1-C_6)$-alkyl, linear or branched $(C_1-C_4)$-alkoxycarbonyl, and linear or branched $(C_1-C_4)$-alkylthio, then A, together with the atoms in common with the pyrrole ring, cannot represent a saturated monocyclic $(C_5-C_8)$-cycloalkyl, each of such groups optionally being substituted by one or two groups selected from linear or branched $(C_1-C_6)$-alkyl, linear or branched $(C_1-C_4)$-alkoxy, and aryl.

2. A compound of claim 1 wherein A represents, together with the atoms in common with the pyrrole ring, a bicyclic $(C_5-C_{12})$-cycloalkyl or monocyclic $(C_5-C_8)$-cycloalkyl which is saturated or mono-unsaturated, optionally substituted by one or more of the groups as defined in claim 1.

3. A compound of claim 1 wherein:

$R_1$ and $R_2$ which are identical, each represents pyridyl optionally substituted by one or more of the groups as defined in claim 1, and A represents, together with the atoms in common with the pyrrole ring, a bicyclic $(C_5-C_{12})$-cycloalkyl or monocyclic $(C_5-C_8)$-cycloalkyl which is saturated or mono-unsaturated, optionally substituted by one or more of the groups as defined in claim 1.

4. A compound of claim 1, which is selected from 1,3-di-(4-pyridyl)-4,7-methano-4,5,6,7-tetrahydro-2H-isoindole or a pharmaceutically-acceptable acid addition salt thereof.

5. A compound of claim 1, which is 1,3-di-(4-pyridyl)-4,7-methano-4,5,6,7-tetrahydro-2H-isoindole dihydrochloride.

6. A compound of claim 1, which is 1,3-di-(5-fluoro-2-pyridyl)-4,7-methano-4,5,6,7-tetrahydro-2H-isoindole.

7. A compound of claim 1, which is 1,3-di-(6-fluoro-3-pyridyl)-4,7-methano-4,5,6,7-tetrahydro-2H-isoindole.

8. A method for treating a living body afflicted with a condition requiring cyclooxygenase-2 inhibitor, and/or interleukine 1β inhibitor, and/or inducible nitric oxyde synthase inhibitor, comprising the step of administering to the living body an amount of a compound of claim 1 which is effective for alleviation of said condition.

9. A pharmaceutical composition useful as a cyclooxygenase-2 inhibitor, and/or interleukine 1β inhibitor, and/or inducible nitric oxyde synthase inhibitor, comprising as active principle an effective amount of a compound as claimed in claim 1, in combination with one or more pharmaceutically-acceptable excipients or carriers.

* * * * *

UNITED STATES PATENT AND TRADEMARK OFFICE
CERTIFICATE OF CORRECTION

PATENT NO.   : 6,114,360
DATED         : September 5, 2000
INVENTOR(S)  : G. De Nanteuil, J. Bonnet, B. Portevin, and C. Tordjman It is certified that error appears in the above-identified patent and that said Letters Patent is hereby corrected as shown below:

Column 8,
Line 66, "-3-pytidylcarbonyl] -" should read: -- 3-pyridylcarbonyl] - --.

Column 22,
Lines 43-45, delete these 3 lines.

Signed and Sealed this

Ninth Day of October, 2001

*Attest:*

*Nicholas P. Godici*

NICHOLAS P. GODICI
*Attesting Officer*   *Acting Director of the United States Patent and Trademark Office*